(12) United States Patent
Duff et al.

(10) Patent No.: US 10,738,020 B2
(45) Date of Patent: Aug. 11, 2020

(54) RECOVERY OF ETHYLENE OXIDE FROM STERILIZATION PROCESS

(71) Applicants: Joseph D. Duff, Louisville, KY (US); Joseph E. Paganessi, Burr Ridge, IL (US)

(72) Inventors: Joseph D. Duff, Louisville, KY (US); Joseph E. Paganessi, Burr Ridge, IL (US)

(*) Notice: Subject to any disclaimer, the term of this patent is extended or adjusted under 35 U.S.C. 154(b) by 0 days.

(21) Appl. No.: 16/746,133

(22) Filed: Jan. 17, 2020

(65) Prior Publication Data

US 2020/0148655 A1 May 14, 2020

Related U.S. Application Data

(63) Continuation-in-part of application No. 15/821,376, filed on Nov. 22, 2017.

(51) Int. Cl.
*C07D 301/32* (2006.01)
*B01D 5/00* (2006.01)

(52) U.S. Cl.
CPC ......... *C07D 301/32* (2013.01); *B01D 5/0051* (2013.01); *B01D 5/0054* (2013.01); *B01D 5/0072* (2013.01)

(58) Field of Classification Search
CPC .. C07D 301/32; B01D 5/0051; B01D 5/0054; B01D 5/0072
See application file for complete search history.

(56) References Cited

U.S. PATENT DOCUMENTS

| | | |
|---|---|---|
| 3,165,539 A | 1/1965 | Lutz |
| 3,372,980 A | 3/1968 | Satas |
| 3,418,338 A | 12/1968 | Gilman et al. |
| 3,549,312 A | 12/1970 | Ernst |
| 3,644,432 A | 2/1972 | Hoch et al. |
| 3,745,092 A | 7/1973 | Vanderwater |
| 3,766,714 A | 10/1973 | Cunningham et al. |
| 3,856,484 A | 12/1974 | Cocuzza et al. |
| 3,948,621 A | 4/1976 | Cocuzza et al. |
| 3,989,461 A | 11/1976 | Skocypec et al. |
| 4,112,054 A | 9/1978 | Feingold et al. |
| 4,130,393 A | 12/1978 | Fox |

(Continued)

OTHER PUBLICATIONS

Ethylene oxide sterilization of medical devices: A Review, by Gisela C.C. Mendes, MD; Teresa R.S. Brandoao, PhD; and Cristina L.M. Silva, PhD., Porto, Portugal, AJIC: American Journal of Infection Control, vol. 35, No. 9, pp. 574-581, Nov. 2007.

*Primary Examiner* — Sean E Conley
(74) *Attorney, Agent, or Firm* — Michael Coblenz

(57) ABSTRACT

The invention relates to a process for the recovery and recycling of ethylene oxide (EO) after use in a sterilization process. The process involves the steps of introducing a mixed gas stream containing EO, nitrogen, oxygen, $CO_2$, water, and a few other trace elements. The system includes integrated EO concentration sensors to determine the concentration of the EO in the gas stream. The system includes a series of compressors to pressurize the gas stream, and chillers or condensers to cool the gas stream to condense the EO out of the gas stream. The system includes temperature and pressure sensors to determine the conditions in the gas stream, and a control system that evaluates the temperature and pressure data and controls the compressors and chillers to achieve the properties to maximize the condensation of EO out of the gas stream.

13 Claims, 4 Drawing Sheets

(56) References Cited

U.S. PATENT DOCUMENTS

| | | |
|---|---|---|
| 4,249,917 A | 2/1981 | Tarancon |
| 4,469,492 A | 9/1984 | Lagana et al. |
| 4,508,927 A | 4/1985 | Bhise et al. |
| 4,529,417 A | 7/1985 | Lagana et al. |
| 4,555,251 A | 11/1985 | Jonsson et al. |
| 4,707,994 A | 11/1987 | Shenoy et al. |
| 4,812,292 A | 3/1989 | Joslyn |
| 4,822,563 A | 4/1989 | Joslyn |
| 4,875,909 A | 10/1989 | Kakimoto et al. |
| 4,954,315 A | 9/1990 | Brahmbhatt |
| 5,069,686 A | 12/1991 | Baker et al. |
| 5,128,101 A | 7/1992 | Boynton |
| 5,149,500 A | 9/1992 | Brahmbhatt et al. |
| 5,261,250 A | 11/1993 | Missimer |
| 5,283,035 A | 2/1994 | Karthaus et al. |
| 5,345,771 A | 9/1994 | Dinsmore |
| 5,472,667 A | 12/1995 | Karthaus et al. |
| 5,529,667 A | 6/1996 | Coffey |
| 5,559,255 A | 9/1996 | Kawabe et al. |
| 5,702,669 A | 12/1997 | Green |
| 5,961,936 A | 10/1999 | Heredia |
| 6,417,411 B2 | 7/2002 | Kakimoto et al. |
| 7,569,710 B1 | 8/2009 | Ozero |
| 8,575,402 B2 | 11/2013 | Bastings et al. |
| 2007/0151451 A1 | 7/2007 | Rekers et al. |
| 2008/0182999 A1 | 7/2008 | Reckers et al. |
| 2009/0143627 A1 | 6/2009 | Van Kruchten et al. |
| 2009/0156867 A1 | 6/2009 | Van Kruchten |
| 2010/0029963 A1 | 2/2010 | Szul et al. |
| 2010/0029964 A1 | 2/2010 | Szul et al. |
| 2010/0063306 A1 | 3/2010 | Osborne et al. |
| 2012/0136178 A1 | 5/2012 | Smaardijk et al. |
| 2012/0197048 A1 | 8/2012 | Van Octrop et al. |

RECOVERY OF ETHYLENE OXIDE FROM STERILIZATION PROCESS

CROSS-REFERENCE TO RELATED APPLICATIONS

This application claims priority to, and is a continuation in part of, U.S. application Ser. No. 15/821,376, filed on Nov. 22, 2017.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

Field of the Invention

The present invention relates to the recovery and recycle of ethylene oxide (EO) from the discharge stream of a sterilization/fumigation chamber. Specifically, the invention provides for the separation of ethylene oxide from moisture and any other impurities followed by the liquefaction of the bulk of the ethylene oxide from the non-condensable gases, and the recycling of liquid ethylene oxide into a storage system.

Description of the Related Art

Sterilization and fumigation are critical to the control and prevention of infectious disease and microbial food spoilage. Without the ability to sterilize pharmaceuticals, drugs, hospital equipment, disposable and reusable medical items, packaging materials, foods, medical devices, books, museum artifacts, scientific equipment, clothing, furs, railcars, aircraft, and beehives (to name a few), the prevention and spread of microorganisms and diseases would be difficult, and in some cases impossible.

The most common form of chemical sterilant used in hospitals, industrial sterilization, and fumigation facilities for sterilizing various plastic, fabric, paper, glass and metal articles consist of 100% ethylene oxide or a blend of ethylene oxide and an inert gas. Typically, ethylene oxide is used as a universal sterilant for heat and moisture sensitive products and as a fumigant to control microorganisms or insects. Estimates show that fifty-six percent (56%) of all medical devices are sterilized using ethylene oxide. The term "sterilant" used in this application means a sterilizing agent capable of completely inactivating or destroying the viability of all types of micro-organisms and insects and their eggs, larvae, and spores contained on or in an object.

Ethylene oxide has many desirable characteristics as a sterilizing agent. Unlike other technologies, such as heat sterilization, radiation, or peroxide, ethylene oxide is a universal sterilant, it is destructive to all forms of organisms, including antibiotic resistance organisms; and it has a relatively rapid action. Additionally, it is non-corrosive and does not damage the substance or equipment during the sterilization process. It is usable at low temperature (in the range of 80-150° F.) and is permeable to many packaging materials as well as most organisms' membranes.

Ethylene oxide does have its issues; the toxicity of Ethylene oxide makes it's a universal sterilant; it also makes it harmful to human exposure. Ethylene oxide is highly toxic, and as a result, many regulations govern the disposal of ethylene oxide. These regulations prevent the bulk release of ethylene oxide into the environment. These regulations allow for the recovery and recycling for future use, providing a sustainable process.

Over the years, hospitals have moved away from Ethylene oxide over environmental concern and employee exposure. That has led to several challenges facing hospitals to sterilize their reusable devices. In the US alone, there have been 23,000 deaths and 2 million illnesses from drug-resistant infections every year. When such an outbreak occurred in Los Angeles in 2015, ethylene oxide was the only sterilant proven effective in controlling the outbreak.

In 2014, the US Environmental Protection Agency classified ethylene oxide as a human carcinogen. This classification has resulted in some states passing laws to prevent the release or lowering the amount of ethylene oxide that is permitted to be released into the atmosphere. On Mar. 26, 2019, the Commissioner of Food and Drugs for the United States Food and Drug Administration issued a statement on the steps the agency was taking to prevent potential medical device shortages and ensure safe and effective sterilization amid a shutdown of a contract ethylene oxide sterilization facility in Illinois. The contract sterilization facility was shut down due to the exposure of ethylene oxide above safe limits to the surrounding populations'. The closure of a small amount of ethylene oxide sterilization capacity has had a large effect on the safe supply of medical devices.

The sterilization process consumes only a small fraction of the ethylene oxide used, which means that a considerable amount of Ethylene Oxide remains after the sterilization process. The bulk of the ethylene oxide has to be converted to ethylene glycol or decomposed to $CO_2$ and water, mitigating the release to the environment. Using current mitigating technologies to convert ethylene oxide in another pollutant is not a solution. There is a need, therefore, for an effective and efficient way to recover un-used Ethylene Oxide from the sterilization process.

For successful utilization of ethylene oxide as a sterilant, the typical process involves exposing products—such as medical equipment—to ethylene oxide in a sealed chamber called a sterilizer. The typical sterilization process encompasses several steps to develop the desired atmosphere for sterilization. The initial step is to develop a non-explosive atmosphere through several vacuum evacuations and re-pressurized cycles with an inert gas to purge the sterilizer atmosphere of oxygen to a predefined concentration. Then the sterilant mixture is generated in the sterilizer by adding moisture, ethylene oxide, inerting gas, and heating the sterilizer to a set temperature. The products are exposed for a pre-defined amount of time to the sterilant mixture to sterilize the products.

The final step in the process is to evacuate the sterilant chamber to remove the sterilant from the atmosphere and the products. To complete this process, many evacuations and re-pressurizing cycles with inert gas or air are performed to wash the products. Lowering the concentration of ethylene oxide from the sterilizer atmosphere to an acceptable level and the removal of residual ethylene oxide is adequate for safe handling of the now sterilized products.

To meet today's medical device manufacturing production demands, there are typically many sterilizing chambers operating in parallel or close to parallel and each operating sterilizer potentially utilizing different sterilizing recipes, leading to different operational temperatures, pressures, operation times and the makeup of the sterilization gas but, not necessarily. Additionally, these recipes are required to be validated on each sterilizer to verify that the recipes are repeatable and meet the FDA specification, and will not harm the product.

The final step in each sterilizer operation is the removal of ethylene oxide (EO) with multiple gas washes to remove residual EO from the sterilizer and the now sterilized medical devices. With multiple sterilizers operating in parallel or close to parallel and each operating with different sterilizing recipes, the concentration of EO originating from multiple sterilizing chambers in a common vent stream is challenging to determine or control without changing how the sterilizers operate, leading to revalidating the process, at great cost.

The Montreal Protocol, finalized in 1987, is a global agreement to protect the stratospheric ozone layer by phasing out the production and consumption of ozone-depleting substances (ODS). Before 2010 most known EO sterilization gas mixtures were premixed in a cylinder of 12% EO and 88% dichlorodifluoromethane (Freon). Water is added to the sterilizing chamber to adjust the relative humidity. After 2010 the makeup of the sterilizing gas changed to atmospheric air, nitrogen, or carbon dioxide as an inert blanketing gas, water, and EO applied in various concentrations. U.S. Pat. Nos. 5,472,667, 5,283,035, 5,261,250, 5,149,500, 5,069,686, 4,954,315, 4,822,563, 4,249,917, 3,989,461, and 3,549,312 all use a sterilizing gas containing a mixture of 12% EO and 88% dichlorodifluoromethane, chlorofluorocarbons (CFC), or hydrochlorofluorocarbons (HCFC) as a part of the sterilization gas mixture. Unfortunately, dichlorodifluoromethane, chlorofluorocarbons (CFC), and hydrochlorofluorocarbons (HCFC) are ozone-depleting substances (ODS), and as a result of the Montreal Protocol banning ODS, none of the inventions disclosed in these patents are usable in the US or anywhere in the world.

Only U.S. Pat. Nos. 5,472,667 and 5,283,035 recognize EO utilized without ODS. U.S. Pat. Nos. 5,472,667, 5,283,035, 5,261,250, 5,149,500, 5,069,686, 4,954,315, 4,822,563, 3,989,461, and 3,549,312, will condense EO and ODS creating a EO/ODS liquid mixture, which as noted is no longer allowed. When condensing EO contained within a multiple species sterilization gases that includes water and ODS, the resulting condensed liquid is a hazardous material that cannot be recycled and has to be disposed of properly. The requirements for the disposal of this now hazardous material result in the reduction or inability to reusing that part of the sterilization gas, reducing the sustainability of EO.

The condensation temperature of the water has some overlay with EO. Depending on the concentration of EO in the gas stream, EO will start to condense at standard atmospheric pressure (14.7 psia) and 0° C. If the gas stream is under pressure higher than standard atmospheric pressure (14.7 psia) and is cooled before the removal of the water, some fraction of EO will be present in the water condensate. This liquid mixture of water and EO is a hazardous material. To process the sterilization gas, a pressure gradient is added to the system in some manner to move the gas from the chamber through the system to be recovered. This combination of pressure and the cooling of the gas stream intended to remove the water leads to some fraction of EO being condensed along with the water. This condensate of water and EO is a hazardous material and has to be disposed of properly. Moreover, the recovery efficiency of the process is reduced, leading to higher costs, greater need for environmental mitigation equipment, and a significant environmental impact.

Removing the water moisture from the gas stream before cooling results in lowing the dew point of water below the dew point of EO in the gas stream, which prevents the water moisture from condensing when the stream is cooled, preventing the contamination and infiltration of water from occurring. U.S. Pat. Nos. 5,149,500 and 5,261,250 do not utilize a precooler or any other means to remove water from the gas stream before condensing the sterilizing gas stream. Moreover, the sterilizing gas contains ODS and is also condensed along with the EO and water, contaminating the EO condensate. U.S. Pat. No. 4,954,315 states that the precooler may be a condenser and is optional. When this optional operation is utilized, the condenser will condense water, EO, and ODS. Additionally, U.S. Pat. No. 4,954,315 takes the additional process step of using a packed column to separate the EO and the ODS for reuse.

U.S. Pat. Nos. 5,472,667 and 5,283,035 removes the water vapor from the gas stream using a desiccant or molecular sieve to remove water vapor, resulting in a gas stream with a water vapor dew point between −80° and −100° C. However, both operate the low-temperature condenser between −80° C. and −130 C. Operating at these temperatures will result in condensing the remaining water vapor in the gas stream, contaminating the EO condensate. However, U.S. Pat. No. 5,472,667 avoid raising the pressure in the system through the use of a vacuum pump at the end of the system. The vacuum pump would lower the operating pressure of the system below standard atmospheric pressure (14.7 psia), resulting in either a lower EO recovery rate or colder condensing temperature to condense the EO to maintain the recovery rate.

U.S. Pat. No. 3,989,461 removes the water vapor from the gas stream using a desiccant. It is unknown what the resulting dew point is of this dried gas stream. The gas stream leaves the desiccant, and then it enters a liquid ring pump using either ethylene or propylene glycol as a sealing liquid. This sealing liquid will come into physical contact with the gas stream, thus contaminating the gas stream with trace amounts of glycol and if present water. This glycol will condense in the condenser resulting in a mixture of EO, ODS, and a trace amount of ethylene, propylene glycol, and water.

Additionally, U.S. Pat. No. 4,822,563 injects steam in the process to move the sterilization gas from the sterilizer to the recovery system. The steam hydrates and raises the relative humidity of the sterilization gas without any means of removal. This is problematic for the process because the compressor used to raise the operation pressure of the system may cause the water to condense out of the gas stream depending on system temperature. Any condensed water will cause erosion in the pump leading to pump failure. Furthermore, this added steam leads to an increase in the amount of water in the condenser, contaminating the EO condensate. U.S. Pat. Nos. 5,149,500 and 5,261,250 don't separate water from the gas stream, leading to water and EO mixture being condensed. U.S. Pat. No. 4,249,917 avoids this issue by absorbing EO and dichlorodifluoromethane using an organic solvent.

In order to separate EO contained within the multiple species sterilization gases U.S. Pat. Nos. 5,472,667, 5,283, 035, 5,261,250, 5,149,500, 5,069,686, 4,954,315, 4,822,563, 4,249,917, 3,989,461, and 3,549,312 all do this in various ways. However, U.S. Pat. No. 5,069,686 does this through many well-known means. For example, it can use a scrubber, a catalytic oxidizer, or other chemical reaction bed. All the previously described technologies convert EO into a different substance. The system is designed first to remove the EO then use membranes to recover the ODS for reuse.

U.S. Pat. Nos. 5,472,667, 5,283,035, 5,261,250, 5,149, 500, 4,954,315, 4,822,563, 3,989,461, and 3,549,312 all separate the EO using a condenser that is operating between −40° C. and −130° C. and do this in various ways. However, the operational pressure of each system is static. Additionally, the pressures for these system ranges from 0 PSIA and an unknown high pressure of a least 22 PSIA based on the limitations described in the patent applications or the described technology. The inability of the system changes the operating pressure or temperature of the condensers to operate under optimal conditions for the separation of EO based on the gas streams concentrations of EO from the multiple incoming species gas limits the amount of EO that can be recovered. U.S. Pat. Nos. 5,283,035, and 3,989,461, attempt to solve this by recirculating the uncondensed gas back into the sterilizer chamber to repeat the process. This process limits the ability to recover EO from many sterilization chambers during gas washing to finalizing the sterilization process operating in or close to parallel. U.S. Pat. Nos. 5,472,667, 5,261,250, 5,149,500, 4,954,315, 4,822, 563, and 3,549,312 only collect what will condense under their operation condition, resulting in lower total collection efficiencies.

It is worth noting, that not all ethylene oxide sterilization processes use inert gas to dilute the initial atmosphere. When not incorporating an inert gas into the sterilization process, the number of initial evacuations required is one. Depending on the product requirements, the vacuum or the pressure levels, the ethylene oxide concentration, number inert gas dilutions, and washes vary. Ethylene oxide sterilization processes are determined using small sterilizer designed to validate the sterilization process before large scale manufacturing of products that require sterilization. Gas washing reduces the concentration of ethylene oxide, making the efficient recovery difficult and energy-intensive after the initial vacuum evacuation.

The use of ethylene oxide as a sterilizing agent is subject to several disadvantages. For example, ethylene oxide is quite flammable and explosive when mixed with air in the correct proportions. To obtain a measure of relief from the explosive and flammability characteristics of ethylene oxide, it is diluted with carbon dioxide, nitrogen, argon, freons, and other chemically inert compounds, thus rendering the mixture nonexplosive. June and Dye described the explosive limits of ethylene oxide-nitrogen mixtures in the publication Plant/Operations Progress, Vol 9, No. 2, April 1990, p73.

Both Fox (U.S. Pat. No. 4,130,393) and Boynton (U.S. Pat. No. 5,128,101) show the use of recompression, storage, and recycling of a mixture of ethylene oxide and an inert gas primarily carbon dioxide or nitrogen. They state that the recycled gas mixture must be monitored to ensure that this gas mixture remains within the non-flammable range. To maintain the oxygen concentration below the desired limit; the storage system must undergo periodic venting of a comparative fraction of the mixture. To maintain the constituents in the gas mixture in the gas phase, inert gas and ethylene oxide are added based on the requirement.

When adding moisture to the sterilizing gas mixture, care must be taken to keep the temperature of the recycle system above the saturation temperature of the moisture due to the high solubility of ethylene oxide in water. Boynton extended the number of permissible recycles before a fractional vent by performing an initial purge of the sterilization/fumigation chamber with an inert gas to reduce the contamination loading of oxygen. Doing this increased the relative ethylene oxide recovery.

In the industrial processes of using ethylene oxides for sterilization and fumigation, over 99% of the ethylene oxide used in the process goes unreacted and is discharged from the sterilization/fumigation chamber. There is a need, therefore, for a system to recover and reuse and recycle this unutilized ethylene oxide.

SUMMARY OF THE INVENTION

The process of the present invention allows for the capture of ethylene oxide by using temperature and pressure to liquefy the ethylene oxide, then separating and recycling the liquefied ethylene oxide from the non-condensable gases. The present invention allows the user to recover then recycle the bulk of the exhausted ethylene oxide, which significantly increases its utilization and thereby reduces the quantity of ethylene oxide required to be on-site. As secondary benefits, The reduction of both feedstock and mitigation costs are significant.

Ethylene oxide ("EO") is frequently used in the fumigation or sterilization process in a solution with other gases, typically a combination of nitrogen, oxygen, and argon, often with carbon dioxide in the solution. In many cases, water vapor moisture is also part of the sterilization/fumigation solution. Except for water vapor, ethylene oxide has a much higher condensation temperature than the other components of the solution. At standard atmospheric pressure (14.7 psia) nitrogen has a condensation temperature of −196° C., argon condenses at −186° C., oxygen condenses at −183° C., and carbon dioxide condenses at −78.5° C. Ethylene oxide, in contrast, begins to condense at 0° C. Because of this, the gaseous solution can be cooled and pressurized to condense out the Ethylene Oxide to remove it from the solution, and thereby recycle the Ethylene Oxide.

The invention uses a series of compressors and chillers or condensers to condense and remove the EO from the gas stream. The invention includes temperature, pressure, and EO sensors to determine the temperature, pressure, and EO concentration of the gas stream. These sensors are in communication with a computerized control system that evaluates the parameters of the gas stream and then adjusts the pressure and temperature to maximize condensation of the EO. The liquefied EO is drained back to an EO holding tank for future sterilization use. This system allows for the recovery and recycle of over 99.5% of the EO in the gas stream.

The advantage of this system is its ability to recover EO for reuse from the vent gas stream of a single or multiple sterilizers operating in parallel or close to parallel. The system uses dynamic pressure and temperature control to change the condenser operational conditions to optimize the separation of EO based on the concentration of EO in the feed stream entering the condenser. The system will not contaminate the condensed EO allowing for reuse, resulting in a sustainable supply of EO. This sustainable supply of EO will lower the environmental impact of the surrounding environment where the ethylene oxide sterilization process is performed.

DETAILED DESCRIPTION OF THE INVENTION

Detailed embodiments of the present invention are disclosed herein. It is to be understood that the disclosed embodiments are merely exemplary of the invention and that there may be a variety of other alternate embodiments. The figures are not necessarily to scale, and some features may be exaggerated or minimized to show details of particular components. Therefore, specified structural and functional details disclosed herein are not to be interpreted as limiting, but merely as a basis for teaching one skilled in the art to employ the varying embodiments of the present invention.

The present invention recovers unused ethylene oxide from the sterilization process by condensing it out of the gaseous solution. It relies on the fact that Ethylene Oxide condenses at a much higher temperature than the other gases in the solution except water. Water is removed from the feedstream at the beginning of the process before the EO is condensed. At standard atmospheric pressure (14.7 psia) nitrogen has a condensation temperature of −196° C., argon condenses at −186° C., oxygen condenses at −183° C., and carbon dioxide condenses at −78.5° C. Ethylene Oxide, in contrast, begins to condense at 0° C. Because of this, the gaseous solution can be cooled and pressurized to condense out the Ethylene Oxide, remove it from the solution, and thereby to recycle the Ethylene Oxide. The system uses a series of chillers and condensers to manipulate the gas stream to achieve the maximum condensation of the Ethylene Oxide from the gaseous stream, and thereby maximize the amount of EO removed and recycled.

Figure 1:
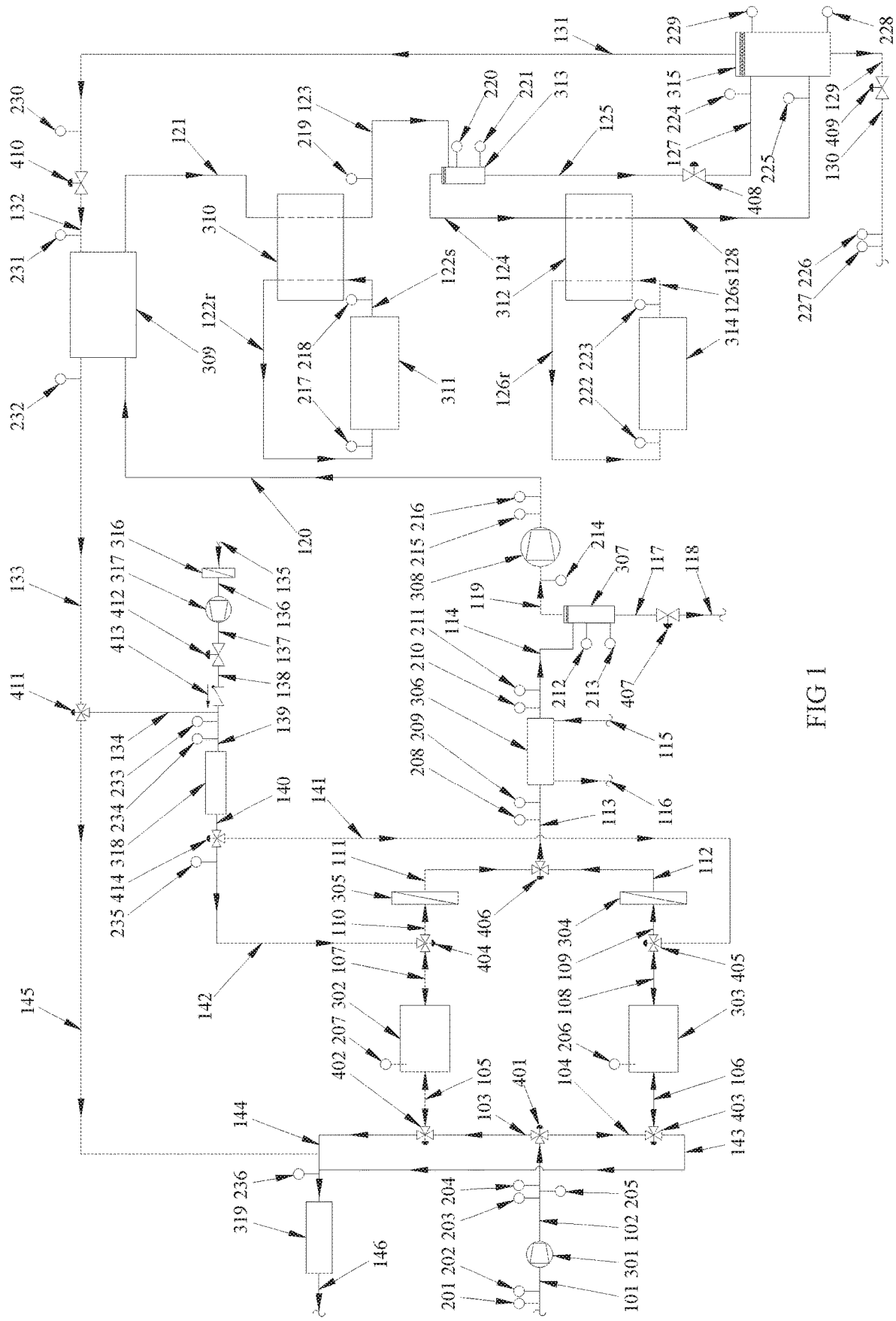
FIG. 1 is a flow chart of a typical ethylene oxide recovery system.

FIG. 1 illustrates the schematic construction of an apparatus for the recovery of ethylene oxide gas from gas sterilization or fumigation process. Feedstream 101 originates at the vented discharge of the sterilization/fumigation chamber vacuum pump or multiple sterilization/fumigation chamber vacuum pumps. As described herein, the gas streams of the system, such as Feedstream 101, are carried through appropriate sized and configured conduit, piping or tubing, so that a reference to "Feedstream 101" means the gas stream of Feedstream 101, as carried through the appropriately sized piping to maintain the desired pressure and temperature. At this point, feedstream 101, the gas stream containing unreacted ethylene oxide is between 60-150° F. and is slightly above atmospheric pressure. Feedstream 101 has a molecular species composition range as present in Table 1.

TABLE 1

| Component | Concentration Range | |
|---|---|---|
| | Lower | Upper |
| Nitrogen | 4.6M % | 87.1M % |
| Oxygen | 0.22M % | 20.8M % |
| Carbon Dioxide | 0M % | 0.04M % |
| Argon | 0.01M % | 0.92M % |
| Water | 0.10M % | 11.9M % |
| Ethylene Oxide | 0.70M % | 82.2M % |

Embedded in Feedstream 101 is Temperature Sensor 201 and Pressure Sensor 202 used to measure the pressure and temperature of the gas in Feedstream 101. Typically, any standard temperature, pressure, or ethylene oxide sensor or measurement device that can accurately determine the temperature, pressure, or concentration of ethylene oxide of the gas stream will work. Feedstream 101 discharges into Booster Pump 301 to increase the gas stream pressure to between 14.7 psia and 30 psia. Because of the increase in pressure, the gas temperature increases by about 50° F. Booster Pump 301 discharges the pressurized gas stream into Feedstream 102, which is directed into the Three-Way Diverter Valve 401. Embedded in Feedstream 102 is a Temperature Sensor 203, Pressure Sensor 204, and Ethylene Oxide Sensor 205.

These sensors are used to measure the pressure, temperature, and concentration of ethylene oxide in the gas stream. The control system (which is not shown) uses the measurements from the Temperature Sensor 201 and 203, and Pressure Sensor 202 and 204, to adjust and control the output from Booster Pump 301 to achieve the desired EO condensation outcome. The control system is a typical and known computerized control system that is in communication with (either by hard-wire of by wi-fi) and controls the hardware in the system—the various sensors, pumps, compressors, chillers, condensers, and valves described herein. The control system obtains relevant data from the sensors, i.e., temperature from the temperature sensors, pressure from the pressure sensors, and EO concentration from the EO sensors. The control system can take immediate temperature, pressure, and EO readings at any point in the system, and make immediate and dynamic adjustments to the disclosed compressors and heat exchangers to achieve the desired temperatures and pressures to achieve maximum condensation of the EO. The control system allows the operators to control the other components of the system, the chillers, condensers, pumps, valves, and so forth. to control the operations of the system, and to manipulate the gas feed streams to the desired pressures and temperatures to achieve the desired level of EO condensation throughout the system to maximize the recovery of EO. Details of the required pressures and temperatures to achieve condensation based on the EO concentration in the feedstream are set out in more detail below. The Three-Way Diverter Valve 401 is controlled by the control system to direct the Feedstream 102 to one of the two parallel Molecular Sieve Dryers 303 or 302 through one of the two Feedstreams 104 or 103, feeding the Three-Way Diverter Valve 402 or 403 and Feedstream 103 or 104, respectively, to feedstreams 105 or 106, which are discharged into the molecular sieve dryers 302 or 303.

The Molecular Sieve Dryers 302 and 303 operate identically and remove water vapor (moisture) from Feedstreams 105 or 106. Molecular Sieve Dryers are known in the industry and are employed to remove moisture from feedstreams 105 or 106 to provide a dried gas stream with a resulting dew point of less than or equal to −80° F. The control system rotates the use of the Molecular Sieve Dryers 302 or 303 based on usage. Each dryer is used for a specified amount of time. When one dryer is in use, the other is regenerating, as described below. Dryer 302 and 303 are embedded with a Temperature Sensor 206 and 207 to measure the temperature of the Molecular Sieve Dryers 302 and 303 to determine the completion of regeneration, as described below.

The Molecular Sieve Dryer 302 and 303 discharge into Feedstream 107 or 108, feeding the Three-Way Diverter Valves 404 or 405. Diverter valves 404 ad 405 are used in the sieve dryer regeneration as described in more detail below. Three-Way Diverter Valve 404 or 405 discharge into Feedstream 109 and 110 and these now dried Feedstreams 109 & 110 discharge into filter 305 or 304 to remove particulate matter from the feedstream. In the removal of particulate matter, any appropriate, common and known filtering technology can be employed, as long as it performs two key functions: One, preventing the Molecular Sieve media from exiting Molecular Sieve Dryer 302 and 303 and entering the system; and two, removing particulate matter from the gas stream resulting in a significant reduction of particle size, thereby mitigating any fouling of equipment downstream by the particulate matter which would have a negative effect on the performance of the equipment.

Filter 305 or 304 discharge the now filtered gas stream into Feedstream 111 and 112 and then discharge into Three-Way Diverter Valve 405. Three-Way Diverter Valve 405 discharges into Feedstream 113 to recombine the gas streams. Embedded in Feedstream 113 is a Temperature Sensor 208 and Pressure Sensor 209 to measure the pressure and temperature of the dehydrated, filtered gas. Feedstream 113 discharges into the first Heat Exchanger 306 which reduces the temperature of the resulting Feedstream 113 between 10 to 85° F. through control of the process coolant from a standard cooling or refrigeration system and supplied by the coolant supply stream 115 and returned through the coolant discharge stream 116, which is 5 to 80° F., depending on the cooling requirements set by the control system. At this point the control system controls the feedstream temperature exiting the first Heat Exchanger 306, discharging into Feedstream 114. Additionally, embedded in Feedstream 114 is a Temperature Sensor 210 and Pressure Sensor 211 to measure the temperature and pressure of Feedstream 114. The temperature and pressure sensors located on either side of the first Heat Exchanger 306 allows the control system to determine the effectiveness of the cooling in the first heat exchanger 306 and allows the control system to adjust the cooling as required to achieve maximum condensation of the EO.

The temperature of Feedstream 114 is chosen by the control system and manipulated by the first heat exchanger 306 to maintain the gas phase ethylene oxide concentration at approximately 40% as measured from ethylene oxide sensor 205 and 214. At this point and forward, the temperatures and pressures of the feed streams need to be controlled throughout the system, to ensure that the Ethylene Oxide does not explode. When the Ethylene Oxide concentration in the feedstream is greater than 40%, the process temperature is reduced to −10° F., thus reducing the Ethylene Oxide concentration below its explosive limit by condensing out some part of the ethylene oxide. The control system and sensors allow the system to adjust in real-time to maintain the required pressure and temperature parameters.

As described herein, the liquid streams, such as Liquid Stream 117, are carried through appropriate conduit, piping or tubing, so that a reference to "Liquid Stream 117" means the liquid stream of Liquid Stream 117 as carried through the appropriately sized piping to maintain the desired pressure and temperature. Feedstream 114 is fed into the first Liquid-Gas Separator 307 to collate any liquid ethylene oxide. Liquid-Gas separators are common and known in the industry. Embedded in the first Liquid-Gas Separator 307 are two Limit Sensors 212, and 213 used to control the amount of liquid ethylene oxide stored in the first Liquid-Gas Separator 307. The use of such limit sensors as known, and typically, any standard limit sensor or measurement device that can be deployed to accurately determine the amount of liquid ethylene oxide in the liquid-gas separator will work and may reduce the number of sensors required for proper operations to one sensor. When the Liquid-Gas Separator 307 reaches a high level of liquid ethylene oxide, the control system opens Valve 407 discharging the first condensed liquid ethylene oxide from the first Liquid-Gas Separator 307 into Liquid Stream 117 through Valve 407 and into Liquid Stream 118. Liquid Stream 118 feeds liquid ethylene oxide to storage either by direct pressure or a liquid pump depending on the operating pressures of both systems. This stored liquid EO can be delivered for storage or reuse. When the level of liquid ethylene oxide reaches a predetermined low level, the control system closes Valve 407, ending the discharge of liquid ethylene oxide. The low level is determined to always allow for the collections of liquid ethylene oxide in first Liquid-Gas Separator 307, thus preventing any gas from escaping the system.

The uncondensed gas from the first Liquid-Gas Separator 307 discharges into Feedstream 119, which is the first discharged gas stream. Embedded in Feedstream 119 is an ethylene oxide sensor 214. Feedstream 119 discharges into the inlet of Compressor 308 where the gas stream pressure is increased to the desired operating pressure based on the required condensing temperature for the current ethylene oxide concentration measured from the ethylene oxide sensor 214 to achieve the desired recovery efficiency, as described in the discussion of FIGS. 2, 3 & 4 below. The maximum stage-wise compression ratio (outlet pressure/inlet pressure) of the system overall, and of the compressor 308 is preferred to be less than 4, because above 6, the Ethylene Oxide mixture has the potential to detonate. There are many different ways to control the outlet pressure of Compressor 308. Any method employed will work as long as it allows for dynamic pressure control from the control system. The pressure sensors 211 and 216 on either side of the compressor 308 allows the control system to control this compression ratio and keep it within acceptable limits. Compressed feedstream 120 is discharged from compressor 308.

The discharge Feedstream 120 is directed to a Countercurrent Heat Exchanger 309 where the bulk of the sensible heat between the incoming hot gas from Feedstream 117 is exchanged with the outgoing cold stream 133 (described in more detail below) thus cooling feedstream 120 and reducing the thermal load on the first condenser 310. Embedded in Feedstream 120, is a Temperature Sensor 215 and Pressure Sensor 216 to measure the pressure and temperature of the gas in stream 120. Countercurrent heat exchanger 309 discharges into Condenser 310 through Feedstream 121.

First Condenser 310 lowers the gas processing temperature of the feedstream 121, thus reducing the Ethylene Oxide concentration by condensing out some part of the ethylene oxide. Condenser 310 may be cooled using either process cooling water or a lower temperature (less than −35° F.) standard refrigeration system using the primary refrigerant or a secondary refrigerant. Condenser 310 discharges a mixture of liquid-vapor into feedstream 123, which is embedded with a Temperature Sensor 219. Temperature sensor 219 measures the gas temperature exiting Condenser 310. The control system utilizes the temperature measurement from 219 to control the gas temperature exiting Condenser 310. The Control system does this by controlling both the flow and temperature, or independently the flow or temperature of the cooling supply stream 122s from the refrigeration system. The cooling supply stream 122s and cooling return stream 122r are embedded with a Temperature Sensor 217 and 218 to measure the temperature of each stream, respectively. To collate any liquid ethylene oxide, feed stream 123 is discharged into the second Liquid-Gas Separator 313.

The second Liquid-Gas Separator 313 includes a High Limit Sensor 220 and a Low Limit Sensor 221. When the Liquid-Gas Separator 313 reaches a high level of liquid ethylene oxide, the control system opens Valve 408 discharging liquid ethylene oxide from the second Liquid-Gas Separator 313 into the second condensed Liquid Stream 125 through Valve 408 and into Liquid Stream 128. To collate the liquid ethylene oxide, Liquid Stream 128 discharges into the third Liquid-Gas Separator 315. When The Liquid-Gas Separator 313 is at a high level of liquid ethylene oxide the Liquid-Gas Separator 313 discharges into Liquid stream 121 and feeds Valve 408 and discharges into Liquid stream 123.

Liquid stream 123 is embedded with a Temperature Sensor 219 to measure the liquid ethylene oxide feeding the third Liquid-Gas Separator 315. The second Liquid-Gas Separator 313 only feeds the third Liquid-Gas Separator 315 when it reaches a high liquid level of stored liquid ethylene oxide. Embedded in the Liquid-Gas Separator 313 are two limit sensors 220 and 221 used to control the amount of liquid ethylene oxide in the Liquid-Gas Separator 313. Typically, any standard limit sensor or measurement device that can accurately determine the amount of liquid ethylene oxide in the Liquid-Gas Separator will work and may reduce the number of sensors required for proper operations to one sensor. When the level of liquid ethylene oxide reaches a low level, the control system closes Valve 408, ending the discharge of liquid ethylene oxide. This low leave is set to always allow for the collections of liquid ethylene oxide in Liquid-Gas Separator 313, preventing any gas from escaping the system.

The second Liquid-gas separator 313 discharges the second uncondensed vapor-phase gas into the second condenser 312 through Feedstream 124. Condenser 312 discharges a mixture of liquid-vapor into feedstream 129. Feedstream 129 is embedded with a Temperature Sensor 225 to measure the temperature of the discharged liquid-vapor stream exiting the second condenser 312. Second Condenser 312 operates at a lower temperature (−35 to −110° F. or lower depending on the non-condensable gases) where additional ethylene oxide is condensed out and is controlled by the control system through control of the Process Coolant Supply 126s and Process Coolant Return 126r.

The Control System controls both the flow and temperature or the flow and temperature independently of the cooling supply stream 126s. The cooling supply stream 126s is supplied by a standard, known, external refrigeration or cooling system. Cooling supply stream 126s and cooling return stream 126r are embedded with a Temperature Sensor 222 and 223 to measure the temperature of streams, respectively. The control system sets the flow and temperature of the cooling supply stream 126s based on the measurement of the Temperature Sensor 225.

To collate any liquid ethylene oxide Liquid-Vapor Stream 128 is discharged into the third Liquid-Gas Separator 315. Third Liquid-Gas Separator 315 discharges into Feedstream 131. Embedded in the third Liquid-Gas Separator 315 are two limit sensors 228 and 229 used to control the amount of liquid ethylene oxide stored in the third Liquid-Gas Separator 315. Typically, any standard limit sensor or measurement device that can accurately determine the amount of liquid ethylene oxide in the liquid-gas separator will work and may reduce the number of sensors required for proper operations to one sensor. When the level of liquid ethylene oxide reaches a low level, the control system closes Valve 409, ending the discharge of liquid ethylene oxide. The low level is set to always allow for the collections of liquid ethylene oxide in third Liquid-Gas Separator 315, preventing any gas from escaping the system. When the third Liquid-Gas Separator 315 reaches a high level of liquid ethylene oxide, the control system opens Valve 409 discharging liquid ethylene oxide from the third Liquid-Gas Separator 315 into second condensed Liquid Stream 129 through Valve 409 and into combined EO Liquid stream 130. Liquid Stream 130 feeds the liquid ethylene oxide storage either by direct pressure or a liquid pump depending on the operating pressures of both systems. Embedded in liquid stream 130 is a Temperature Sensor 226 and Pressure Sensor 227 to measure the pressure and temperature of the liquid stream being discharged into storage. The second liquid-gas separator 313 previously discharged condensed liquid EO to the third liquid-gas separator 315, so all remaining liquid EO is in a single stream.

The Liquid-Gas Separator 315 discharges any uncondensed ethylene oxide remaining in the gas stream along with all non-condensable gases in the stream into the second discharge Feedstream 131. At this point, there should be very little EO remaining in the gas stream. The use of the three chillers/condensers in series allows for the stepped down cooling of the gas stream and the removal of typically over 95.5% of the original EO in the feedstream The remaining non-condensable gases are fed to Flash Valve 410. Embedded into Feedstream 131 is a pressure sensor 230 used to measure the pressure in the gas stream. Flash valves are known and discharge a pressurized gas to a lower pressure, which results in rapid cooling. Flash Valve 410 discharges into supercooled Feedstream 132 producing a lower-pressure and super-cooled gas stream, and discharged into Concurrent Heat Exchanger 309. The use of the supercooled gas of feedstream 132 allows the system to cool feedstream 120 in the concurrent heat exchanger 309 as described above. This use of the supercooled feedstream 132 to cool feedstream 120 removes the need for additional cooling thus reducing the overall energy requirements of the system, and thus also reducing the cost to operate the system. Embedded into Feedstream 132 is a temperature sensor 231 to measure the temperature of the gas stream. Concurrent Heat Exchanger 309 discharges the reheated gas into Feedstream 133. Embedded into Feedstream 133, is an ethylene oxide sensor 232 used to measure the concentration of ethylene oxide in Feedstream 133. At this point the EO concentration should be below 0.05%.

Feedstream 133 is now directed to, and used for regeneration of the sieve dryers through the Three-way Diverter Valve 411. If there is no present need for regeneration the three-way divertere valve 411 directs feedstream 133 to a discharge feedstream 145, which sends the gas stream to the EO mitigation system 319. Based on the need to regenerate the Molecular Sieve Dryers 302 or 303 the gas from Valve 411 is fed into Feedstream 134 mixing with the Feedstream 139 to produce Dryer Purge Gas 139, which is run through the Molecular Sieve Dryers in the opposite direction of the flow of the feedstreams 105 or 106 in order to purge the excess moisture from the Molecular Sieve Dryers to regenerate them. The system adds extra atmospheric air to the dryer purge gas 139 which is brought in at feedstream 135. Feedstream 135 feed atmospheric air into filter 316, to remove any particulate matter, and the filtered air stream 136 is discharged into Compressor 317 which compresses the atmospheric air to the same pressure as the dryer purge gas 139, and then discharges Feedstream 137 to feed Valve 412. Valve 412 regulates the flow to the appropriate rate directed into stream 138. The filtered and compressed air in Feedstream 138 is discharged into Directorial Flow Valve 413, which is then fed into mixed gas Feedstream 139. Directional Flow Valve 413 is employed to control the direction of flow thus preventing any backflow resulting from the mixing of gas from Feedstream 134 and Feedstream 139. Embedded into Feedstream 139 are Pressure Sensor 233 and Temperature Sensor 234.

Feedstream 139 discharges into Heater 318 to increase the Dryer Purge Gas temperature to between 250 and 400° F., to improve the purging of the molecular sieve dryers, before being discharged into stream 140 and fed into Three-Way Valves 414. The control system determines which stream to feed, 141 or 142, based on the need to flush the moisture-laden Molecular Sieve Dryers's (either 302 or 303) of moisture. The operation of flushing and thereby regenerating the moisture-laden Molecular Sieve Dryers's is identical except for the path through the system. As noted above, when a molecular sieve dryer is in use drying feedstream 105 or 106, the other is being regenerated by the backflow dryer purge gas.

Feedstream 141 or 142 feeds either Three-Way Valves 404 or 405 depending on which Molecular Sieve Dryers 302 or 303 is currently employed to dehydrate the incoming feedstream 105 or 106 from the discharge of the sterilization/fumigation chamber vacuum pump as described above. Three-Way Valves 404 or 405 discharge into Feedstream 107 or 108, which flow in the opposite direction as Feedstream 105 or 106, and feed to Molecular Sieve Dryers 302 or 303. Molecular Sieve Dryers 302 or 303 to purge and regenerate them, and then discharge into the conduit or piping of Feedstream 105 or 106 feeding Three-Way Valves 402 or 403. Three-Way Valves 402 or 403 discharge into Feedstream 142 or 143 and feed into Ethylene Oxide Mitigation System 319. The Molecular Sieve Dryer 302 or 303 is regenerated by flushing the excess moisture by means of the counterflow of the purge gas and through achieving the desired bed temperature by means of heating the purge gas, wherein the desired bed temperature is determined by the control system through the measurement from the embedded Temperature Sensor 207 or 208. Once the desired molecular sieve bed temperature is reached, the flush with dryer purge gas hot air is terminated, and the molecular sieve bed is cooled with ambient air which is brought in from feedstream 139 followed by a cooling purge with the cool non-condensable gas originating from Feedstream 133, which is not heated with Heater 318, but fed into the system unheated in order to cool the molecular sieve beds (302 or 303). After the purge gas has been run through the respective molecular sieve dryers 302 or 303, the gas is discharged at 143 or 144 and into the Ethylene Oxide Mitigation System 319. The Ethylene Oxide Mitigation System 319 is external to the present invention. At this point, the final Feedstreams 143 or 144 have between zero and 0.5% ethylene oxide. This remaining small amount of EO is mitigated in a number of different ways. The two most common are through the use of oxidation or scrubbers, both of which are well known in the industry. The mitigated gas stream is now vented from the Mitigation System 319 into discharge feedstream 146 and into the atmosphere. Other mitigation technologies can also be used.

Figure 2:
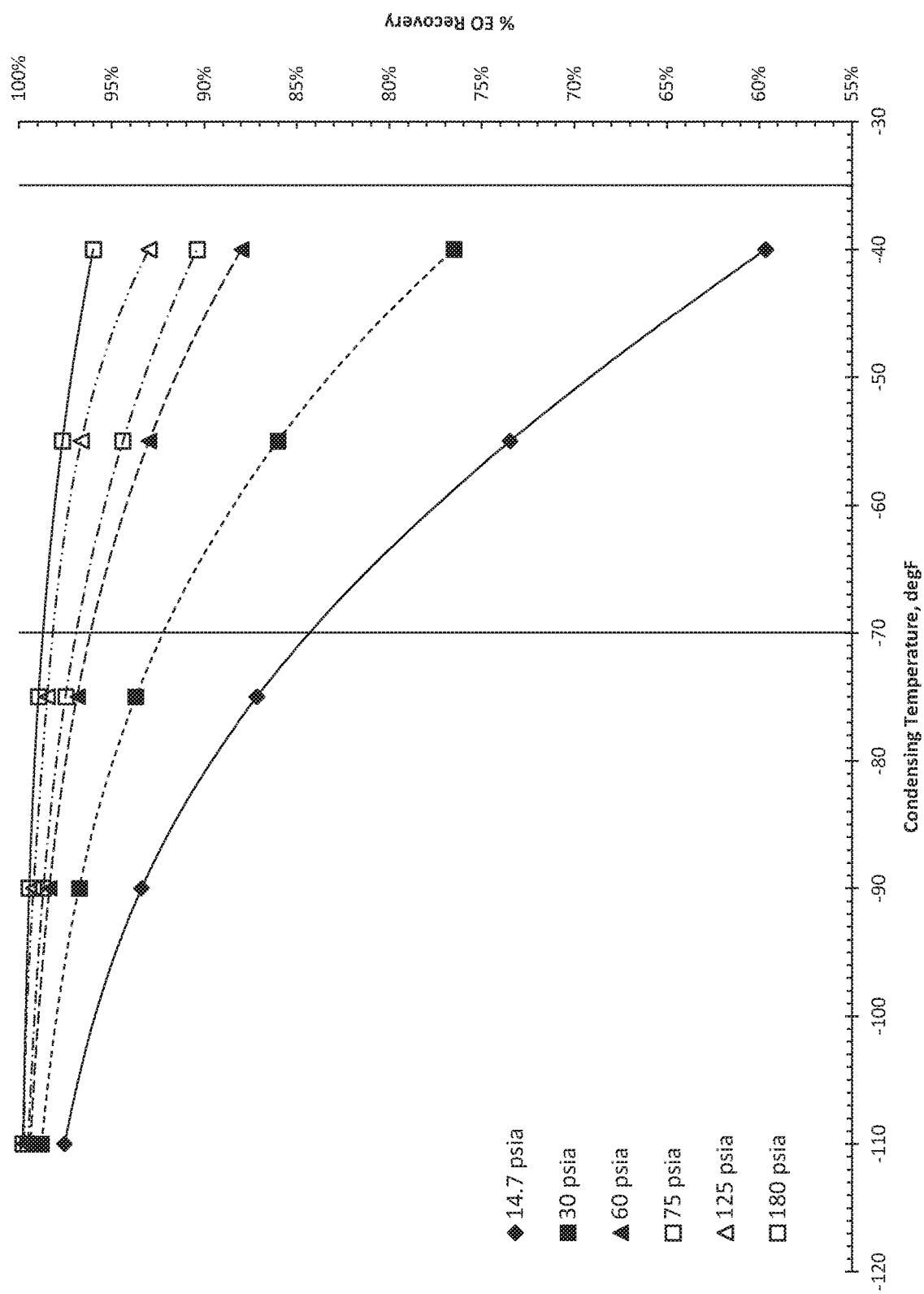
FIG. 2 is a chart showing ethylene oxide recovery versus condensing temperature and operating pressure for Feed A.

Different concentrations of the initial feedstock, which is brought in at feedstream 101 require different temperatures and pressures to maximize the percentage of Ethylene Oxide recovery. The control system operates dynamically, constantly taking measurements of the EO concentration at the noted locations with the EO sensors in the system, and constantly adjusting the pressure by means of the Booster Pump 301 and the Compressor 308, and adjusting the temperature by means of the First Feat Exchanger 306, the Countercurrent Heat Exchanger 309, the First Condenser 310 and the Second Condenser 312 to achieve maximum EO condensation. FIG. 2 is the potential ethylene oxide recovery versus system pressure and temperature for feedstock A, as shown in Table 2.

TABLE 2

| Component | Stream, M % | | | |
| --- | --- | --- | --- | --- |
|  | 1 | 2 | 3 | 4 |
| Nitrogen | 4.63% | 60.64% | 74.77% | 77.45% |
| Oxygen | 1.24% | 16.27% | 20.06% | 20.78% |
| Carbon Dioxide | 0.00% | 0.03% | 0.03% | 0.04% |
| Argon | 0.06% | 0.72% | 0.89% | 0.92% |
| Water | 11.85% | 2.81% | 0.53% | 0.10% |
| Ethylene Oxide | 82.22% | 19.53% | 3.71% | 0.70% |

Figure 3:
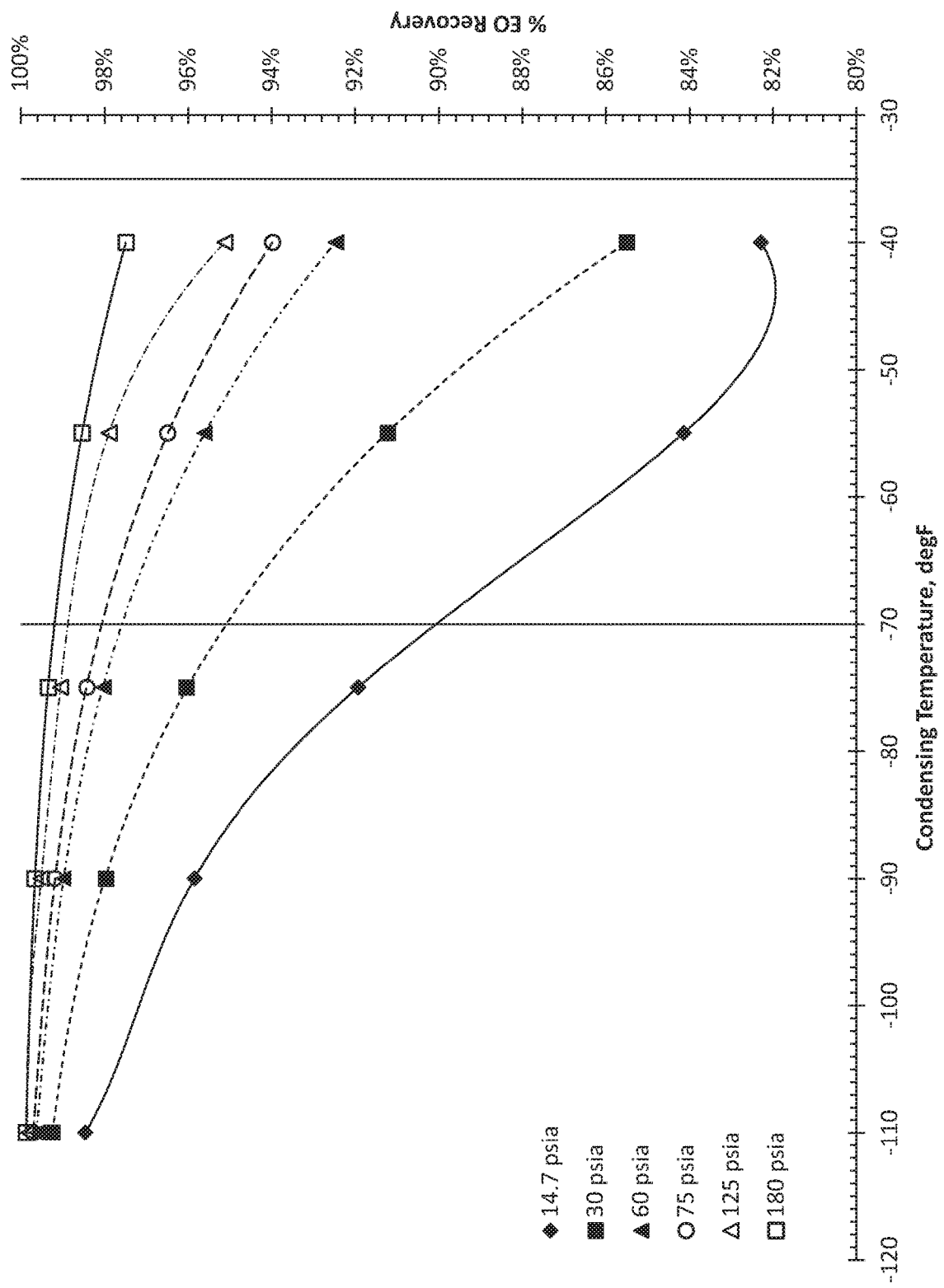
FIG. 3 is a chart showing ethylene oxide recovery versus condensing temperature and operating pressure for Feed B.

As can best be understood through FIG. 2, the condensing temperature of the Ethylene Oxide varies according to the pressure, and this affects the percentage of Ethylene Oxide recovery. So, for example, at 14.7 psia (standard atmospheric pressure) the maximum amount of Ethylene Oxide is recovered at a temperature of −100° F., while at −40° F. only about 60% of the EO is recovered. FIG. 3 is the potential ethylene oxide recovery versus system pressure and temperature for feedstock B, as shown in Table 3.

TABLE 3

| Component | Stream, M % | | |
| --- | --- | --- | --- |
|  | 1 | 2 | 3 |
| Nitrogen | 59.99% | 87.14% | 81.34% |
| Oxygen | 0.70% | 0.22% | 13.49% |
| Carbon Dioxide | 0.00% | 0.00% | 0.02% |
| Argon | 0.03% | 0.01% | 0.60% |
| Water | 7.14% | 2.30% | 0.83% |
| Ethylene Oxide | 32.14% | 10.33% | 3.72% |

Figure 4:
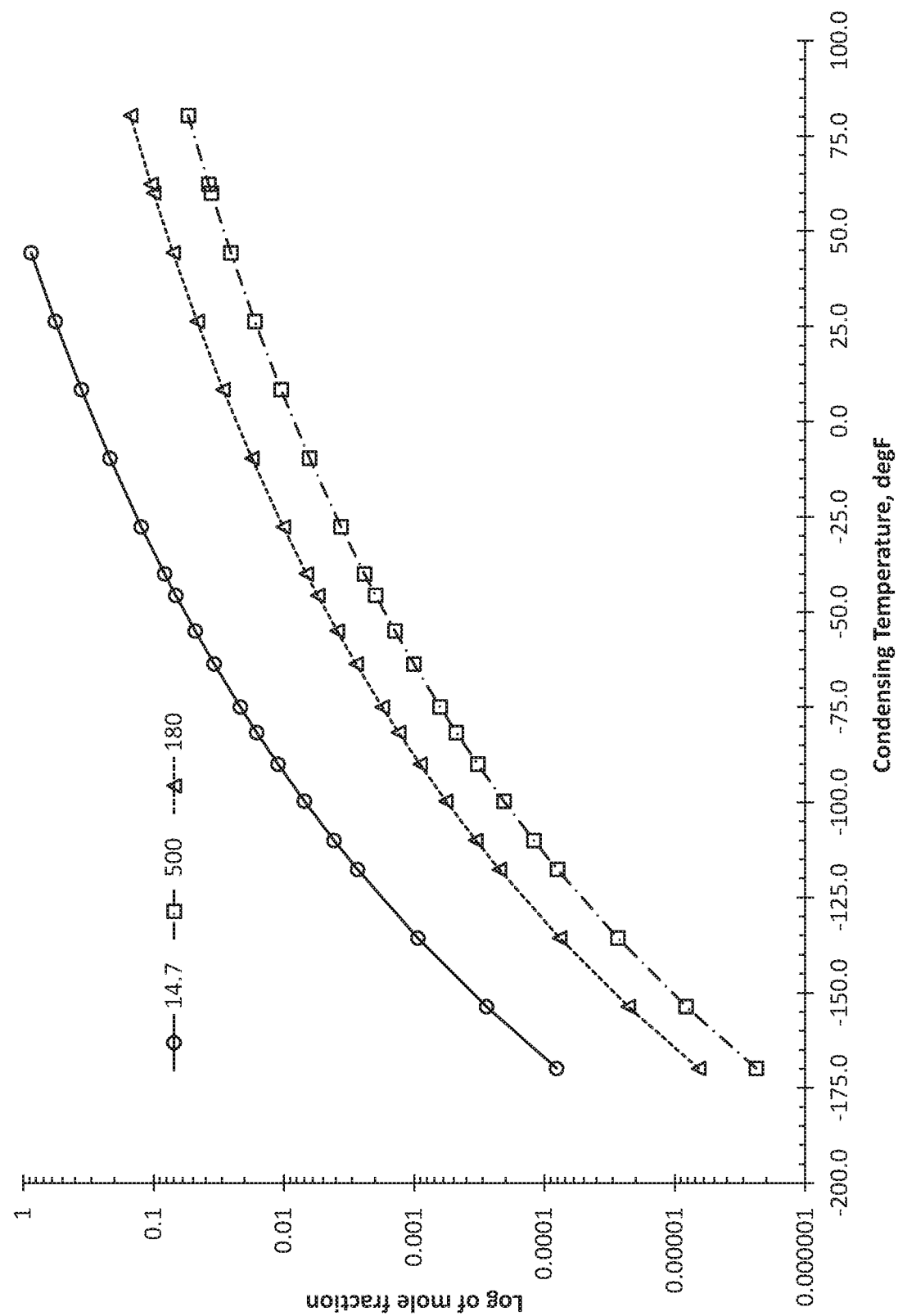
FIG. 4 is a chart showing the minimum mole fraction (EO Concentration/100) in the feed stream required to initiate condensation as a function of temperature and pressure.

As can be seen in both FIG. 3 and FIG. 4, the percentage of EO recovered increases as the pressure increases or the temperature decreases. It is possible to achieve maximum EO recovery by decreasing the temperature and increasing the pressure in one cycle, but this would require specialized and expensive compression and refrigeration equipment. The current system achieves these results in steps, and with the use of standard compressors and condensers or chillers. In the preferred embodiment this is with the use of the two compressors and four heat exchangers as described herein.

Additionally, the use of the cooled feedstream 132 to cool feedstream 120 reduces the need for additional cooling equipment, thus reducing system cost as well as operational costs. The control system will know the concentration of the initial feedstream 101 being discharged from the sterilization process, and can control the pressurization and cooling throughout the system. At each step the control system will take the EO concentration of the gas stream and adjust the pressure, early in the process, and then adjust the cooling in the later stages of the process, to achieve maximum condensation and removal of the EO from the gas stream.

FIG. 4 shows the minimum mole fraction of Ethylene Oxide needed in the gas stream to initiate condensation of Ethylene Oxide. One can readily find the vapor pressure of Ethylene Oxide as a function of temperature in the relevant technical literature. The mole fraction allows one to calculate the partial pressure of Ethylene Oxide in the gas stream. The control system will have this information, and will use it to adjust the pressure and temperature of the system. If the partial pressure is greater than the vapor pressure at that temperature, the constituent condenses out. Ethylene Oxide dew points for Feeds A and B are respectively 7.85° F. and 41.9° F. Any value above this minimum mole fraction value would allow for condensing Ethylene Oxide down to that level thus allowing one to separate liquid Ethylene Oxide from a mixture of non-condensable, gaseous Ethylene Oxide and liquid Ethylene Oxide. Presented in Table 4 are the estimated condenser temperatures required to achieve 99.5% Ethylene Oxide recovery for Streams A and B at stated system pressures.

TABLE 4

| Pressure psia | Stream A | Stream B |
|---|---|---|
| | Temperature, ° F. | |
| 15 | −139 | −123 |
| 30 | −128 | −111 |
| 45 | −121 | −103 |
| 90 | −108 | −88 |
| 135 | −100 | −79 |
| 180 | −94 | −72 |

This data is integrated into the control system so that the control system can evaluate the concentration of EO in the feed stream and dynamically adjust the pressure or temperature or both in real-time to achieve the maximum condensation of EO.

There are several significant advantages to employing this process. The increased utilization of ethylene oxide from low to high percentage yields a substantial reduction in the need to convert ethylene oxide into a hazardous product for proper disposal. The system recovers over 99.5% of the EO, which can be recovered, recycled, and reused for future sterilization needs. This means there is only a tiny fraction remaining that must be recovered or mitigated by other, less environmentally friendly processes The use of this system results in reduced purchasing of ethylene oxide, which lowers operating expenses, cylinder changes reducing the risk of accidental ethylene oxide release, cutting the needed for on-site storage of ethylene oxide in inventory, reducing the amount on-site storage of ethylene glycol and water waste storage, shipping and receiving of feedstock delivery, and waste disposal.

Parts List:
101—initial vented discharge gas feedstream; 102—pressurized discharge gas feedstream; 103—gas stream to dryer 1; 104—gas stream to dryer 2; 105—post valve gas stream to dryer 1; 106—post valve gas stream to dryer 2; 107—dried gas stream 1; 108—dried gas stream 2; 109—dried gas stream to filter 2; 110—dried gas stream to filter 1; 111—filtered gas stream 1; 112—filtered gas stream 2; 113—rejoined filtered gas stream; 114—first chilled gas stream; 115—first chiller intake gas stream; 116—first chiller outflow gas stream; 117—first liquid ethylene oxide EO liquid discharge stream; 118—first liquid EO stream to recycle; 119—first liquid-gas separator discharged gas stream; 120—second compressed gas stream; 121—after concurrent heat exchanger gas stream; 122$s$ & 122$r$—refrigeration streams for first chiller; 123—after first condenser gas stream; 124—after second liquid-gas separator gas stream; 125—second liquid EO stream after second liquid-gas separator; 126$s$ & 126$r$—refrigeration streams for second condenser; 127—second liquid EO stream after control valve; 128—after second condenser gas stream; 129—third liquid EO stream after third liquid-gas separator; 130—third liquid EO stream after control valve; 131—gas discharge stream after third liquid-gas separator; 132—discharge gas stream after flash valve; 133—discharge gas stream after concurrent heat exchanger; 134—discharge gas stream after three-way diverter valve for regeneration of sieve dryers; 135—outside air intake air stream; 136—outside air stream after filter; 137—outside air stream after compressor; 138—outside air after control valve; 139—regeneration air and gas mix after directional valve; 140—regeneration air and gas mix after heater; 141—regeneration mix to second dryer; 142—regeneration mix to first dryer; 143—regeneration mix after second dryers; 144—regeneration mix after first dryer; 145—discharge gas feedstream after regeneration three-way valve; 146—discharge mix after recycle; 201—discharge gas temperature sensor; 202—discharge gas pressure sensor; 203—pressurized discharge gas temperature sensor; 204—pressurized discharge gas pressure sensor; 205—pressurized discharge gas EO sensor; 206—temperature sensor in dryer 2; 207—temperature sensor in dryer 1; 208—filtered gas stream temperature sensor; 209—filtered gas stream pressure sensor; 210—chilled gas stream temperature sensor; 211—chilled gas stream pressure sensor; 212—first liquid-gas separator upper limit sensor; 213—first liquid-gas separator lower limit sensor; 214—post liquid-gas separator EO Sensor; 215—Second Compressed gas stream Temperature Sensor; 216—Second Compressed gas stream Pressure Sensor; 217—Second Condensed gas stream Input Temperature sensor; 218—Second Condensed gas stream Output Temperature sensor; 219—Post Second Condenser condensed gas stream Temperature sensor; 220—second liquid-gas separator upper limit sensor; 221—second liquid-gas separator lower limit sensor; 222—Third Condenser input gas stream Temperature sensor; 223—Third Condenser Output gas stream Temperature sensor; 224—Post $2^{nd}$ L-G Liquid Temp Sensor; 225—Post Third Condenser gas stream Temperature Sensor; 226—post $3^{rd}$ L-G Liquid Temperature Sensor; 227—Post $3^{rd}$ L-G Liquid Pressure Sensor; 228—Third liquid-gas separator Lower Limit Sensor; 229—Third liquid-gas separator Upper Limit Sensor; 230—Pre-Flash Valve gas stream Pressure Sensor; 231—Post Flash Valve gas stream Temp Sensor; 232—Post Concurrent heat exchanger gas stream EO Sensor; 233—Post Mix gas and air stream Pressure Sensor; 234—Post Mix gas and air stream Temperature Sensor; 235—Purge Gas Temperature Sensor; 236—Final Discharge gas EO Sensor; 301—Boost Pump; 302—Molecular Sieve Dryer 1; 303—Molecular sieve dryer 2; 304—Filter 2; 305—Filter 1; 306—First Chiller; 307—First Liquid-Gas Separator; 308—Compressor; 309—Concurrent Heat Exchanger; 310—First Condenser (chiller);

311—First Refrigeration system for first condenser; 312—Second Condenser (chiller); 313—Second Liquid-Gas Separator; 314—Second Refrigeration system for second condenser; 315—Third Liquid-Gas Separator; 316—Outside Air Filter; 317—Outside air compressor; 318—Regeneration air heater; 319—Venter Gas EO Recycling system; 401—Pre-dryer Three-way diverter valve; 402—three-way valve to dryer 1; 403—three-way valve to drier 2; 404—regeneration 1 three-way valve; 405—regeneration 2 three-way valve; 406—post filter rejoin three-way valve; 407—First Liq-Gas discharge valve; 408—Second Liq-Gas discharge valve; 409—Third Lig-Gas discharge valve; 410—Flash Valve; 411—Regeneration direction 3-way valve; 412—Outside Air directional; 413—Outside Air control valve; 414—Regeneration counterflow 3-way.

The present invention is well adapted to carry out the objectives and attain both the ends and the advantages mentioned, as well as other benefits inherent therein. While the present invention has been depicted, described, and is defined by reference to particular embodiments of the invention, such reference does not imply a limitation to the invention, and no such limitation is to be inferred. The depicted and described embodiments of the invention are exemplary only and are not exhaustive of the scope of the invention. Consequently, the present invention is intended to be limited only by the spirit and scope of the claims, giving full cognizance to equivalents in all respects.

We claim:

1. A method of recovering ethylene oxide from the discharge gas stream of a sterilization chamber using ethylene oxide in the sterilization process, said method of recovering ethylene oxide comprising the steps of:
    pressurizing said discharge gas stream to create a pressurized gas stream;
    drying said pressurized gas stream to remove water moisture thereby creating a dried gas stream;
    filtering said dried gas stream to remove any particulate impurities thereby creating a filtered gas stream;
    cooling said filtered gas stream to a temperature to condense ethylene oxide out of said filtered gas stream, thereby creating a first condensed liquid ethylene oxide stream and a first discharged gas stream;
    collecting said first condensed liquid ethylene oxide stream for recycle and reuse; and
    treating and discharging said first discharged gas stream.

2. The method of recovering ethylene oxide of claim 1 including the further steps of
    introducing temperature sensors into the discharge gas stream, the pressurized gas stream, the dried gas stream, and the filtered gas stream to determine the temperatures of these gas streams;
    introducing pressure sensors into the discharge gas stream, the pressurized gas stream, the dried gas stream, and the filtered gas stream to determine the pressure of these gas streams;
    introducing ethylene oxide sensors into the discharge gas stream, the pressurized gas stream, the dried gas stream, and the filtered gas stream to determine the ethylene oxide content of these gas streams;
    wherein the pressure, temperature, and ethylene oxide content of the gas streams determines cooling requirements for the dried gas stream to achieve maximum ethylene oxide condensation.

3. The method of recovering ethylene oxide of claim 2 including the further steps of
    pressurizing said discharge gas stream with a compressor;
    cooling said filtered gas stream with a chiller; and
    controlling said compressor and said chiller with a control system, wherein said control system obtains temperature readings from said temperature sensors, pressure readings from said pressure sensors, and ethylene oxide readings from said ethylene oxide sensors to determine the pressure to pressurize the discharge gas stream and the temperature to cool the filtered gas stream to achieve maximum condensation of the ethylene oxide.

4. The method of recovering ethylene oxide of claim 3, wherein said control system takes immediate readings and makes immediate adjustments to the pressure and temperature depending on the ethylene oxide content of the pressurized gas stream to achieve maximum condensation of the ethylene oxide.

5. The method of recovering ethylene oxide of claim 1 including the further steps of
    further condensing and cooling said first discharged gas stream to condense ethylene oxide out of said first discharged gas stream, thereby creating a second condensed liquid ethylene oxide stream and a second discharged gas stream;
    collecting said second condensed liquid ethylene oxide stream for reuse;
    further cooling second discharged gas stream to condense ethylene oxide out of the second discharged gas stream, thereby creating a third condensed liquid ethylene oxide stream and a third discharged gas stream;
    collecting the third condensed liquid ethylene oxide stream for reuse;
    treating and discharging said third discharged gas stream;
    thereby removing over 99.5% of the ethylene oxide from the initial discharge gas stream.

6. The method of recovering ethylene oxide of claim 5 including the further steps of
    directing said second discharge gas stream to a heat exchanger;
    directing said third discharged gas stream to said heat exchanger to cool said second discharged gas stream, thereby reducing the cooling load requirements of said method.

7. The method of recovering ethylene oxide of claim 6 including the further steps of:
    drying said pressurized gas stream in a sieve dryer;
    heating said third discharged gas stream;
    directing said third discharged gas stream to said sieve dryer;
    counterflowing said third discharged gas stream through said sieve dryer to remove moisture build up and regenerate said sieve dryer.

8. A method of recovering ethylene oxide from the vented gas stream of a sterilization chamber using ethylene oxide in the sterilization process, said method comprising the steps of:
    pressurizing said vented gas stream to an operating pressure of between 14.7 and 30 psia;
    drying said vented gas stream to remove water moisture to create a dried gas stream;
    filtering said dried gas stream to remove any particulate impurities to create a filtered gas stream;
    cooling the filtered gas stream to a first temperature to condense a first portion of ethylene oxide out of said pressurized gas stream, thereby creating a first condensed liquid ethylene oxide stream and a first discharge gas stream;
    collecting the first condensed liquid ethylene oxide stream for reuse;

pressurizing the first discharged gas stream to create a second pressurized gas stream;

cooling the second pressurized gas stream to a second temperature to condense a second portion of ethylene oxide out of the second pressurized gas stream, thereby creating a second condensed liquid ethylene oxide stream and a second discharge gas stream;

collecting the second condensed liquid ethylene oxide stream for reuse;

further cooling and condensing the second discharge gas stream to condense the remaining ethylene oxide out of the second discharge gas stream, thereby creating a third condensed liquid ethylene oxide stream and a third discharge gas stream;

collecting the third condensed ethylene oxide stream for reuse;

treating and discharging the third discharge gas stream;

thereby removing over 99.5% of the ethylene oxide from the initial sterilizer discharge gas stream.

9. The method of recovering ethylene oxide of claim 8 including the further steps of introducing temperature sensors into the vented gas stream, the pressurized gas stream, the dried gas stream, the filtered gas stream, the first discharge gas stream, the second discharge gas stream, and the third discharge gas stream to determine the temperatures of these gas streams;

introducing pressure sensors into the vented gas stream, the pressurized gas stream, the dried gas stream, the filtered gas stream, the first discharge gas stream, the second discharge gas stream, and the third discharge gas stream to determine the pressure of these gas streams;

introducing ethylene oxide sensors into the vented gas stream, the pressurized gas stream, the dried gas stream, the filtered gas stream, the first discharge gas stream, the second discharge gas stream, and the third discharge gas stream to determine the ethylene oxide content of these gas streams;

providing a control system in communication with said temperature sensors, said pressure sensors, and said ethylene oxide sensors to monitor said temperature, pressure, and ethylene oxide content;

wherein the pressure, temperature, and ethylene oxide content of the gas streams determines the cooling requirements of the pressurized gas stream, the first discharge gas stream, and the second discharge gas to achieve maximum ethylene oxide condensation.

10. The method of recovering ethylene oxide of claim 9 including the further steps of pressurizing said vented gas stream with a compressor;

drying said pressurized gas stream with a molecular sieve dryer;

filtering said dried gas stream with a filter;

cooling said filtered gas stream with a chiller;

cooling said first discharge gas stream with a first heat exchanger;

cooling said second discharge gas stream with a second heat exchanger;

controlling said compressor, said chiller, said first heat exchanger, and said second heat exchanger with said control system, wherein said control system obtains temperature readings from said temperature sensors, pressure readings from said pressure sensors, and ethylene oxide readings from said ethylene oxide sensors to determine the pressure to pressurize the filtered gas stream, the temperature to cool the pressurized gas stream, the first discharge gas stream, and the second discharge gas stream to achieve maximum condensation of ethylene oxide.

11. The method of recovering ethylene oxide of claim 10 including the further steps of directing said second discharge gas stream to said second heat exchanger;

directing said third discharged gas stream to said second heat exchanger to cool said second discharged gas stream, thereby reducing the cooling load requirements of said method.

12. The method of recovering ethylene oxide of claim 10 including the further steps of:

drying said pressurized gas stream in a sieve dryer;

heating said third discharged gas stream;

directing said third discharged gas stream to said sieve dryer;

counterflowing said third discharged gas stream through said sieve dryer to remove moisture build up and regenerate said sieve dryer.

13. The method of recovering ethylene oxide of claim 12 including the further steps of providing a first dryer and a second dryer, wherein said first dryer and second dryer are monitored and controlled by said control system;

providing a three-way valve controlled by said control system, wherein an intake valve accepts said vented gas stream, a first outlet valve directs said vented gas stream to said first dryer, and a second outlet valve directs said vented gas stream to said second dryer;

determining whether said first dryer or second dryer is in an optimal drying state or in a regeneration state;

directing said vented gas stream to either the said first dryer or said second dryer depending on which is in the optimal drying state.

* * * * *